United States Patent
Fagan et al.

(10) Patent No.: US 9,181,209 B2
(45) Date of Patent: *Nov. 10, 2015

(54) PROCESS FOR THE PRODUCTION OF FURFURAL

(71) Applicant: E I DU PONT DE NEMOURS AND COMPANY, Wilmington, DE (US)

(72) Inventors: Paul Joseph Fagan, Wilmington, DE (US); Ronnie Ozer, Arden, DE (US); Eric J. Till, Newtown Square, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,375

(22) Filed: Dec. 28, 2012

(65) Prior Publication Data

US 2013/0172581 A1    Jul. 4, 2013

Related U.S. Application Data

(60) Provisional application No. 61/580,711, filed on Dec. 28, 2011, provisional application No. 61/580,714, filed on Dec. 28, 2011.

(51) Int. Cl.
  *C07D 311/92*    (2006.01)
  *C07D 307/50*    (2006.01)

(52) U.S. Cl.
  CPC ................ *C07D 307/50* (2013.01)

(58) Field of Classification Search
  CPC .................................................. C07D 307/50
  USPC ........................................................ 549/489
  See application file for complete search history.

(56) References Cited

U.S. PATENT DOCUMENTS

| | | | |
|---|---|---|---|
| 2,536,732 A | | 1/1951 | Dunlop |
| 2,559,607 A | * | 7/1951 | Dunning et al. ............. 549/489 |
| 2,750,394 A | | 6/1956 | Peniston |
| 4,088,660 A | | 5/1978 | Puurunen |
| 4,154,744 A | | 5/1979 | Hamada |

(Continued)

FOREIGN PATENT DOCUMENTS

| | | |
|---|---|---|
| CN | 100999677 A | 7/2007 |
| CN | 101367782 A | 2/2009 |

(Continued)

OTHER PUBLICATIONS

Karinen (ChemSusChem, 2011, 4, 1002-1016.*
Weingarten (Green Chem., 2010, 12, 1423-1429.*
International Search Report, PCT International Application No. PCT/US2012/071936, Mailed Apr. 26, 2013.
Orozco, "Dilute Acid Hydrolysis of Cellulose and Cellulosic Bio-Waste Using a Microwave Reactor System", Sep. 2007, Institution of Chemical Engineers, vol. 85 (B5), p. 446-449.

(Continued)

*Primary Examiner* — Andrew D Kosar
*Assistant Examiner* — Raymond Convington

(57) ABSTRACT

Furfural is produced by mixing an aqueous feedstock solution containing $C_5$ sugar and/or $C_6$ sugar with a heated, high boiling, water-miscible solvent, such as sulfolane, and a soluble acid catalyst. Furfural product and water are distilled off through a multistage distillation column, leaving non-volatile solvent behind. Typical furfural yields with sulfolane as the reaction solvent are about 80% at as high as 99% conversion. Also, certain by-products (e.g., humins) solubilized in the reaction solvent can be precipitated by addition of water or aqueous feedstock solution and then removed by filtration, thereby providing a convenient and effective way of removing these undesirable byproducts from the reaction mixture.

14 Claims, 2 Drawing Sheets

(56) References Cited

U.S. PATENT DOCUMENTS

| | | | |
|---|---|---|---|
| 4,366,322 | A | 12/1982 | Raymond |
| 4,503,023 | A | 3/1985 | Breck |
| 4,533,743 | A | 8/1985 | Medeiros |
| 4,897,497 | A | 1/1990 | Fitzpatrick |
| 5,608,105 | A | 3/1997 | Fitzpatrick |
| 5,859,263 | A | 1/1999 | Ghorpade |
| 6,441,202 | B1 | 8/2002 | Lightner |
| 6,518,440 | B2 | 2/2003 | Lightner |
| 6,743,928 | B1 | 6/2004 | Zeitsch |
| 7,572,925 | B2 | 8/2009 | Dumesic |
| 8,277,521 | B2 | 10/2012 | Gruter |
| 8,314,260 | B2 | 11/2012 | Gruter |
| 8,389,749 | B2 | 3/2013 | Dumesic |
| 8,399,688 | B2 | 3/2013 | Dumesic |
| 2003/0032819 | A1 | 2/2003 | Lightner |
| 2007/0298477 | A1 | 12/2007 | Kratochvil |
| 2008/0033187 | A1 | 2/2008 | Zhao |
| 2008/0033188 | A1 | 2/2008 | Dumesic |
| 2009/0124839 | A1 | 5/2009 | Dumesic |
| 2009/0131690 | A1 | 5/2009 | Gruter |
| 2009/0156841 | A1 | 6/2009 | Sanborn |
| 2009/0194407 | A1 | 8/2009 | Tang |
| 2009/0306415 | A1 | 12/2009 | Gruter |
| 2010/0048924 | A1 | 2/2010 | Kilambi |
| 2010/0058650 | A1 | 3/2010 | Gruter |
| 2010/0083565 | A1 | 4/2010 | Gruter |
| 2010/0212218 | A1 | 8/2010 | Gruter |
| 2010/0218415 | A1 | 9/2010 | Gruter |
| 2010/0218416 | A1 | 9/2010 | Gruter |
| 2010/0299991 | A1 | 12/2010 | Gruter |
| 2010/0317879 | A1 | 12/2010 | Zhao |
| 2011/0065159 | A1 | 3/2011 | Raines |
| 2011/0071306 | A1 | 3/2011 | Robinson |
| 2011/0144359 | A1* | 6/2011 | Heide et al. .......... 549/489 |
| 2012/0108829 | A1* | 5/2012 | de Jong et al. ......... 549/489 |
| 2012/0111714 | A1 | 5/2012 | Court |
| 2012/0157697 | A1 | 6/2012 | Burket |
| 2013/0017579 | A1 | 1/2013 | Luterbacher |

FOREIGN PATENT DOCUMENTS

| | | |
|---|---|---|
| CN | 101486695 A | 7/2009 |
| CN | 101130530 A | 11/2010 |
| EP | 2033958 A1 | 3/2009 |
| GB | 799603 A | 8/1958 |
| GB | 838957 A | 6/1960 |
| JP | 02-108682 A | 4/1990 |
| JP | 12065468 A | 10/1998 |
| JP | 2007196174 A | 8/2007 |
| WO | 0047569 A1 | 8/2000 |
| WO | 2009155297 A1 | 12/2009 |
| WO | 2011063500 A1 | 6/2011 |

OTHER PUBLICATIONS

NFOA for U.S. Appl. No. 13/729,526, Jun. 19, 2015.

E. I. Fulmer et al., The Production of Furfural From Xylose Solutions by Means of Hydrochloric Acid-Sodium Chloride Systems, Department of Chemistry, Iowa, Journal of Physical Chemistry, vol. 40 (1936), pp. 133-141.

C. Liu et al., The Enhancement of Xylose Monomer and Xylotriose Degradation by Inorganic Salts in Aqueous Solutions at 180oC, Carbohydrate Research, vol. 341 (2006), pp. 2550-2556.

G. Marcotullio et al., Chloride Ions Enhance Furfural Formation From D-Xylose in Dilute Aqueous Acidic Solutions, Green Chemistry (2010), The Royal Society of Chemistry, pp. 1-8.

F. Tao et al., Efficient Process for the Conversion of Xylose to Furfural With Acidic Ionic Liquid, Can. J. Chem., vol. 89 (2011), pp. 83-87.

Gairola et al., Hydrothermal Pentose to Furfural Conversion and Simultaneous Extraction With SC—CO2, Kinetics and Application to Biomass Hydrolysates, Bioresource Technology, vol. 123 (2012), pp. 592-598.

Kawamoto et al., Catalytic Pyrolysis of Cellulose in Sulfolane With Some Acidic Catalysts, J Wood Sci, vol. 53 (2007), pp. 127-133.

Suzuki et al., Dehydration of Xylose Over Sulfated Tin Oxide Catalyst: Influences of the Preparation Conditions on the Structural Properties and Catalytic Performance, Applied Catalysis A: General, vol. 408 (2011), pp. 117-124.

Starr et al., High Sulfidity Pulping in Aqueous Sulfolane, TAPPI Alkaline Pulping Conference Preprints (1975), pp. 195-198.

Clermont, Delignification of Aspen Wood With Aqueous Sulfolane Solutions, TAPPI, vol. 53, No. 12 (1970), pp. 2243-2245.

Chheda et al., Production of 5-Hydroxymethylfufual and furfural by dehydration of biomass-derived mono- and polysaccharides, Green Chemistry, 2007, 342-350, 9, The Royal Society of Chemistry.

Mamman et al., Furfural: Hemicellulose/xylose-derived biochemical, Biofuels, Bioproducts & Biorefining, 2008, 438-453, Wiley Interscience.

Vazquez et al., Hydrolysis of Sorghum Straw using Phosphoric Acid: Evaluation of Furfural Production, Bioresource Technology, 2007, 3053-3060, 98, Elsevier.

Amiri et al., Production of furans from rice straw by single-phase and biphasic systems, Carbohydrate Research, 2010, 2133-2138, vol. 345.

Weingarten et al., Kinetics of furfural production by dehydration of xylose in a biphasic reactor with microwave heating, Green Chemistry, The Royal Society of Chemistry, 2010, 1423-1429, vol. 12.

Zhao et al., Metal Chlorides in Ionic Liquid Solvents Convert Sugars to 5-Hydroxymethylfurfural, Science, 2007, 1597-1600, vol. 316.

Dias et al., Dehydration of xylose into furfural over micro-mesoporous sulfonic acid catalysts, Journal of Catalysis, 2005, 414-423, vol. 229.

\* cited by examiner

PROCESS FOR THE PRODUCTION OF FURFURAL

This application claims priority under 35 U.S.C. §119(e) from, and claims the benefit of, U.S. Provisional Application No. 61/580,711, filed Dec. 28, 2011; and U.S. Provisional Application No. 61/580,714, filed Dec. 28, 2011; each of which is herein incorporated by reference.

FIELD OF THE INVENTION

A method for the production of furfural from $C_5$ and $C_6$ sugars is provided.

BACKGROUND OF THE INVENTION

Furfural and related compounds are useful precursors and starting materials for industrial chemicals for use as pharmaceuticals, herbicides, stabilizers, and polymers. The current furfural manufacturing process utilizes biomass such as corn cob, sugar cane bagasse, switchgrass or wood waste as a raw material feedstock for obtaining glucose, glucose oligomers, cellulose, xylose, xylose oligomers, arabinose, hemicellulose, and other $C_5$ and $C_6$ sugar monomers, dimers, oligomers, and polymers.

The hemicellulose and cellulose are hydrolyzed under acidic conditions to their constituent sugars, such as glucose, xylose, mannose, galactose, rhamnose, and arabinose. Xylose, which is a pentose (i.e., a $C_5$ monosaccharide) is the sugar present in the largest amount in hemicellulose. In a similar aqueous acidic environment, the $C_5$ sugars are subsequently dehydrated and cyclized to furfural. Under similar conditions, $C_6$ sugars can be hydrolyzed and converted in low yields to furfural.

In a process disclosed by John W. Dunning et al. in U.S. Pat. No. 2,559,607, aqueous pentose (1.5-10%) was converted to furfural under pressure using sulfuric acid (1.5-5 wt %) and temperatures from 140° C. to 165° C. Three different methods were used to separate the furfural product from the pentose solution. In the first two, furfural was removed by extraction into toluene; in the third method, the furfural was removed by steam stripping. Dunning et al. claimed yields as high as 80% using the first two methods and slightly lower yields using the third method. These yields were based on the amount of xylose converted in the process, which typically required reprocessing the soluble xylose stream several times to get up to only about 50% xylose conversion.

In a process disclosed by Andrew P. Dunlop (U.S. Pat. No. 2,536,732), furfural was produced in yields of up to 82% where aqueous xylose solutions were fed to solvents substantially insoluble in water (restricted to the class of solvents alkylated benzenes, polyhalogenated benzenes, and chlorinated biphenyls), wherein the reaction pot was a biphasic reaction mixture of aqueous xylose and solvent as separate phases. Yields of 82% were obtained at 0.39 parts of xylose per 100 parts of water solution, but only 49% yield was obtained at higher concentrations of xylose feed (9.38 parts of xylose per 100 parts of aqueous solution).

In a process disclosed by David J. Medeiros et al. in U.S. Pat. No. 4,533,743, aqueous pentose solution was reacted at high temperature and pressure in the presence of a mineral acid catalyst to maximize furfural yield and selectivity. The process utilized a plug flow reactor and a combination of four conditions: The concentration of pentose in the pentose-aqueous feed solution before entry into the reactor was between 1 and 10 percent by weight of the aqueous solution before the addition of acid; the concentration of the mineral acid in the reactor was between 0.05 and 0.2 normality before entry into the reactor; the reactor was operated at a temperature between 220° C. and 300° C.; and the residence time of the pentose in the reactor was between 0.5 and 100 seconds. The reactor pressure was high enough to prevent vaporization of the aqueous solutions at the high temperatures used, between about 1000 and 2000 psi (6.895 and 13.79 MPa). In one configuration of the process, furfural produced from a xylose stream was separated with a water immiscible extraction solvent. The yield of furfural was 66% after one pass. Because incomplete conversion of the xylose took place, the aqueous solution could be recycled for additional yield. The selectivity of the xylose converted was 73%. Faster flow rates increased selectivity at the expense of lowered conversion, suggesting that maximum yields using multiple cycles would reach 80-85%. In a second configuration, the aqueous xylose solution was mixed with an immiscible solvent, toluene, before reaction. The conversion was 98% and the yield was 71%.

In a process disclosed by Takeshi Suzuki, et al. (Applied Catalysis A: General, 2011, Vol. 408, pp 117-124), solid acid catalysts were employed to convert xylose to furfural; solid acid catalyst processes described in the art require high reaction temperature and pressure and/or supercritical solvent to attain the selective production of furfural with a high yield, and are often deactivated by collection of humins on the catalyst.

In a process disclosed by Haruo Kawamoto, et al. (J. Wood Science, 2007, Vol. 53, pp 127-133) pyrolysis of the $C_6$ sugar oligosaccharide cellulose in sulfolane with an acid catalyst at 200° C. and with steam yielded furfural in ca. 27% yield; without steam or water added yields of furfural were ≤20%.

There remains a need for a process to produce furfural at both high yield and high conversion, capable of operation in a batch or continuous mode, and which allows for removal of soluble humin byproduct in a batch or continuous mode. It is also desirable that such a process be carried out without the need for high pressure equipment.

SUMMARY OF THE INVENTION

In an aspect of the invention, there is a process comprising:
(a) providing a reactor comprising a distillation column disposed on top of a reaction vessel, wherein the reaction vessel contains an acid solution comprising a soluble acid catalyst in a water-miscible organic solvent;
(b) bringing an aqueous feedstock solution into contact with the acid solution in the reaction vessel for a residence time sufficient to produce a mixture of water and furfural, wherein the aqueous feedstock solution comprises $C_5$ sugar, $C_6$ sugar or a mixture thereof, and wherein the contents of the reaction vessel are at a temperature in the range of 100-250° C. and a pressure in the range of 0.0001-0.21 MPa;
(c) removing the mixture of water and furfural from the top of the distillation column; and
(d) adding water or the aqueous solution to at least a portion of the contents of the reaction vessel comprising organic solvent, acid catalyst, water, unreacted sugars and non-volatile byproducts to precipitate water-insoluble byproducts and removing the precipitated water-insoluble byproducts.

In another aspect, there is a process comprising the steps of:
a) providing a water-miscible organic solvent and a soluble acid catalyst in a reaction vessel, wherein the boiling point of the solvent is higher than about 100° C.;

b) providing an aqueous feedstock solution comprising: at least one $C_5$ sugar, at least one $C_6$ sugar, or a mixture of at least one $C_5$ sugar and at least one $C_6$ sugar;

c) adding the feedstock solution to the reaction vessel to form a reaction mixture wherein
   i) the temperature of the reaction mixture is between about 100° C. and about 250° C.,
   ii) the reaction mixture pressure is between 0 MPa and about 0.21 MPa, and
   iii) the feedstock, organic solvent, and catalyst are in contact for a time sufficient to effect a reaction to produce furfural and water;

d) removing vapors of furfural and water from the reaction mixture via reflux through a multistage distillation column;

e) condensing and collecting a solution of furfural and water; and f) recovering the furfural from the solution of furfural and water collected in step e).

In one embodiment of the invention disclosed herein, the contents of the reaction vessel are heated to a temperature between about 100° C. and about 250° C. before step c).

In a further embodiment of the invention disclosed herein, the process further comprises the steps of:

g) diluting the remaining contents of the reaction vessel, or a portion thereof, in a mixing chamber with water or with an aqueous feedstock solution comprising: at least one $C_5$ sugar, at least one $C_6$ sugar, or a mixture of at least one $C_5$ sugar and at least one $C_6$ sugar, thereby precipitating water-insoluble byproducts;

h) removing the byproducts precipitated in step g), and i) feeding the solution remaining after step h) back to the reaction vessel.

BRIEF DESCRIPTION OF THE DRAWINGS

Various features and/or embodiments of this invention are illustrated in drawings as described below. These features and/or embodiments are representative only, and the selection of these features and/or embodiments for inclusion in the drawings should not be interpreted as an indication that subject matter not included in the drawings is not suitable for practicing the invention, or that subject matter not included in the drawings is excluded from the scope of the appended claims and equivalents thereof.

DETAILED DESCRIPTION

Definitions

Figure 1:
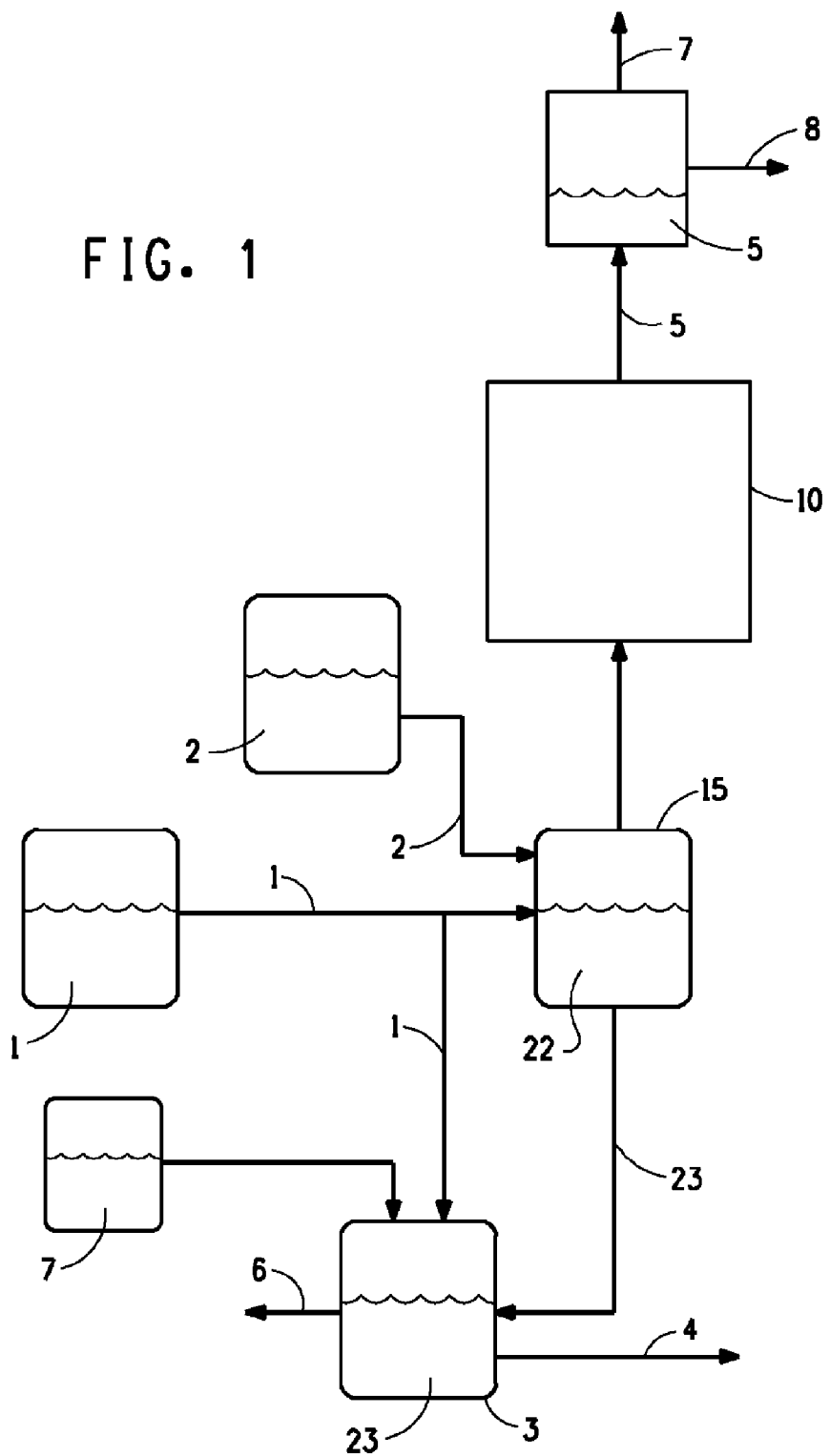
FIG. 1 is a schematic illustration of an exemplary reactor configuration used in the production of furfural in a batch mode, in accordance with various embodiments of the present invention.

The methods described herein are described with reference to the following terms.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; some examples are xylose, arabinose, lyxose and ribose. A hexose is a monosaccharide having six carbon atoms; some examples are glucose and fructose. Disaccharide molecules (e.g., sucrose, lactose, and maltose) consist of two covalently linked monosaccharide units. As used herein, "oligosaccharide" molecules consist of about 3 to about 20 covalently linked monosaccharide units.

As used herein, the term "$C_n$ sugar" includes monosaccharides having n carbon atoms; disaccharides comprising monosaccharide units having n carbon atoms, and oligosaccharides comprising monosaccharide units having n carbon atoms. Thus, "$C_5$ sugar" includes pentoses, disaccharides comprising pentose units, and oligosaccharides comprising pentose units.

As used herein, the term "hemicellulose" refers to a polymer comprising $C_5$ and $C_6$ monosaccharide units. Hemicellulose consists of short, highly branched chains of sugars. In contrast to cellulose, which is a polymer of only glucose, a hemicellulose is a polymer of five different sugars. It contains five-carbon sugars (usually D-xylose and L-arabinose) and six-carbon sugars (D-galactose, D-glucose, and D-mannose). Hemicellulose can also contain uronic acid, sugars in which the terminal carbon's hydroxyl group has been oxidized to a carboxylic acid, such as, D-glucuronic acid, 4-O-methyl-D-glucuronic acid, and D-galacturonic acid. The sugars are partially acetylated. Typically, the acetyl content is 1 to 10% by weight of the total weight of the hemicellulose. Xylose is typically the sugar monomer present in hemicellulose in the largest amount.

As used herein, the term "high boiling" denotes a solvent having a boiling point above about 100° C. at 0.101 MPa.

As used herein, the term "organic" denotes carbon-containing compounds with the following exceptions: binary compounds as the carbon oxides, carbides, carbon disulfide, etc.; ternary compounds such as metallic cyanides, metallic carbonyls, phosgene, carbonyl sulfide; and metallic carbonates such as calcium carbonate and sodium carbonate.

As used herein the term "water-miscible organic solvent" refers to an organic solvent that can form a monophasic solution with water at the temperature at which the reaction is carried out.

As used herein, the term "catalytic amount" means a sub-stoichiometric amount of catalyst relative to a reactant.

As used herein, the term "selectivity" refers to the moles of furfural produced, divided by the moles of xylose transformed to products over a particular time period.

As used herein, the term "organic acid" means an organic compound having acidic properties; some examples are acetic acid, formic acid, and methane sulfonic acid.

As used herein, the term "mineral acid" means an inorganic acid, as distinguished from organic acid. Some examples are sulfuric acid, nitric acid, phosphoric acid, and hydrochloric acid.

As used herein, the term "heteropolyacid" denotes an oxygen-containing acid with P, As, Si, or B as a central atom which is connected via oxygen bridges to W, Mo or V. Some examples are phosphotungstic acid, molybdophosphoric acid.

As used herein the term "humin(s)" refers to dark, amorphous byproduct(s) resulting from acid induced sugar and furfural degradation.

In an embodiment, there is a process for the production of furfural comprising providing a reactor configuration comprising a distillation column disposed on top of a reaction vessel, wherein the reaction vessel contains an acid solution comprising a soluble acid catalyst in a water-miscible organic solvent. FIG. 1 shows a schematic illustration of an exemplary reactor configuration comprising a distillation column 10 disposed on top of a reaction vessel 15, wherein the distillation column comprises a condenser and wherein the reaction vessel 15 contains an acid solution 2 comprising a soluble acid catalyst and a water-miscible organic solvent.

The water-miscible organic solvent has a boiling point higher than about 100° C. at atmospheric pressure. Examples of suitable water-miscible organic solvents include without limitation: sulfolane, polyethylene glycol, isosorbide dimethyl ether, isosorbide, propylene carbonate, poly(ethylene glycol)dimethyl ether, adipic acid, diethylene glycol, 1,3-propanediol, gamma-butyrolactone, and gamma-valerolactone. In one embodiment, the water-miscible organic solvent is PEG 4600, PEG 10000, PEG 1000, gamma-valerolactone, gamma-butyrolactone, isosorbide dimethyl ether, propylene carbonate, adipic acid, poly(ethylene glycol)dimethyl ether, isosorbide, Cerenol™ 270 (poly(1,3-propanediol), Cerenol™ 1000 ((poly(1,3-propanediol)), or diethylene glycol. In one embodiment, the water-miscible organic solvent is sulfolane.

The soluble acid catalyst is water-soluble and comprises a mineral acid, a heteropolyacid, an organic acid, or a combination thereof. In one embodiment, the acid catalyst is a mineral acid comprising sulfuric acid, phosphoric acid, hydrochloric acid, or a combination of these. In another embodiment, the acid catalyst is a heteropolyacid comprising phosphotungstic acid, molybdophosphoric acid, or a combination of these. In other embodiment, the acid catalyst is an organic acid comprising oxalic acid, formic acid, acetic acid, an alkyl sulfonic acid, an aryl sulfonic acid, a halogenated acetic acid, a halogenated alkylsulfonic acid, a halogenated aryl sulfonic acid, or a combination of these. An example of a suitable alkyl sulfonic acid is methane sulfonic acid. An example of a suitable aryl sulfonic acid is toluenesulfonic acid. An example of a suitable halogenated acetic acid is trichloroacetic acid. An example of a suitable halogenated alkylsulfonic acid is 1,1,2,2-tetrafluoroethanesulfonic acid. An example of a suitable halogenated aryl sulfonic acid is fluorobenzenesulfonic acid.

The soluble acid catalyst is present in the water-miscible organic solvent in the range of 0.01-12 weight % or 0.01-5 weight % or 0.1-1.5 weight %, based on the total weight of the acid plus solvent. In some embodiments, the acid is present in the solvent at a weight percentage between and optionally including any two of the following values: 0.01, 0.05, 0.10, 0.15, 0.20, 0.50, 1.0, 1.5, 2.0, 3.0, 4.0, 5.0, 6.0, 7.0, 8.0, 9.0, and 10 weight percent. The optimal amount of acid catalyst will be affected by what specific solvent is used and the reaction conditions and is readily determined by one of skill in the art.

The process for the production of furfural also comprises, as shown in the FIG. 1, bringing an aqueous feedstock solution 1 into contact with the acid solution 2 to form a reaction mixture 22 in the reaction vessel 15 for a residence time sufficient to produce a mixture 5 comprising water 7 and furfural 8. In an embodiment, the aqueous feedstock solution 1 comprises $C_5$ sugar, $C_6$ sugar or a mixture thereof. In another embodiment, the reaction solution is at a temperature in the range of 90-250° C. and a pressure in the range of 0.0001-0.21 MPa.

The aqueous feedstock comprises at least one $C_5$ sugar, at least one $C_6$ sugar, or a mixture of at least one $C_5$ sugar and at least one $C_6$ sugar. Examples of suitable $C_5$ sugars (pentoses) include without limitation xylose, arabinose, lyxose and ribose. Examples of suitable $C_6$ sugars (hexoses) include without limitation glucose, fructose, mannose, and galactose.

In one embodiment, the aqueous feedstock solution comprises xylose. In other embodiment, the aqueous feedstock solution comprises glucose. In another embodiment, the aqueous feedstock solution comprises xylose and glucose.

The total amount of sugar ($C_5$ sugar, $C_6$ sugar, or a mixture thereof) present in the aqueous feedstock solution in the range of 0.1-99 weight or 1-50 weight % or 5-35 weight % or 5-10 weight %, based on the total weight of the aqueous feedstock solution. In some embodiments, the $C_5$ sugar is present in the feedstock solution at a weight percentage between and optionally including any two of the following values: 0.1, 0.5, 1, 2, 3, 4, 5, 6, 7, 8, 9, 10, 15, 17, 19, 21, 23, 25, 30, 35, 40, 45, 50, 55, 60, 65, 70, 75, 80, 85, 90, 95, and 99 weight percent.

The temperature of the reaction mixture 22 in the reaction vessel 15 is between about 100-250° C. or 100-190° C. or 120-180° C. In some embodiments, the temperature of the reaction mixture is between and optionally including any two of the following values: 100, 110, 120, 130, 140, 150, 160, 170, 180, 190, 200, 210, 220, 230, 240, and 250° C.

The reaction is carried out at a pressure less than about 0.21 MPa, thus eliminating the need for the high-pressure equipment used in some earlier processes. In an embodiment, the reaction vessel 15 and the distillation column 10 are kept at a pressure less than 0.21 MPa or less than 0.11 MPa or less than 0.050 MPa. The process for the production of furfural further comprises, as shown in the FIG. 1, removing the mixture 5 comprising water 7 and furfural 8 from the top of the distillation column 10. As the reaction proceeds, vapors of furfural 8 and water 7 are removed from the reaction mixture 22 via reflux through a multistage distillation column 10, condensed, and collected as a solution 5 comprised of furfural 8 and water 7. The use of staging in the distillation process allows more efficient stripping of furfural 8 away from the reaction mixture 22 and minimizes loss of water miscible solvent overhead. This increases furfural yield by driving the reaction toward completion and by minimizing formation of byproducts.

The process for the production of furfural further comprises, as shown in the FIG. 1, adding water 7 or the aqueous feedstock solution 1 to at least a portion 23 of the contents of the reaction vessel 15 comprising organic solvent, acid catalyst, water, unreacted sugars and nonvolatile byproducts in a mixing zone 3 to precipitate water-insoluble byproducts 4 and removing the precipitated water-insoluble byproducts 4 from the remaining solution 6.

In one embodiment, the process is a batch mode, with reference to FIG. 1, the reaction vessel 15 is charged initially with an acid solution 2 comprising a high boiling, water-miscible solvent and a catalytic amount of soluble acid. The contents of the reaction vessel 15 are heated to the reaction temperature. An aqueous feedstock solution 1 containing $C_6$, and/or $C_6$ sugar is added over time to the hot reaction vessel 15. The sugar undergoes chemical transformation to furfural 8, which, along with water 7 from the aqueous feedstock solution 1 and water produced by the reacton, is then removed from the reaction mixture 22 via reflux through a multistage distillation column 10 equipped with a condenser. This minimizes the residence time of furfural 8 in the acidic environment of the reaction mixture 22 and thereby minimizes its degradation. The furfural 8 is separated from the water 7 and purified by any convenient methods known in the art, and the product furfural 8 is isolated. The water is either recycled to the source of the aqueous feedstock solution or is released from the process. After the completion of reaction, non-volatile components are left in the reaction vessel 15 including, but not limited to, the high boiling water-miscible solvent, soluble acid, unreacted sugar, and unwanted byproducts such as humins. The water-insoluble byproducts can be removed by diluting at least a portion 23 of the contents of the reaction vessel 15 with water 7 or an aqueous feedstock solution 7 which results in the precipitation of humins 4. The solution 6 is separated from the humins, and can be recycled into another batch process. The ratio of added water or aqueous feedstock solution to reaction vessel contents, referred to herein as the "dilution ratio," can be from about 0.5:1 up to 100:1 by volume. A higher dilution ratio causes more humins to precipitate, and a lower dilution ratio results in less precipitate. In an embodiment, the ratio is from about 3:1 to about 20:1 by volume. In an embodiment, the ratio is from about 1:1 to about 10:1 by volume. In some embodiments, the dilution ratio is between and optionally including any two of the following values: 0.5:1, 1:1, 2:1, 3:1, 4:1, 5:1, 6:1, 7:1, 8:1, 9:1, 10:1, 12:1, 14:1, 16:1, 18:1, 20:1, 25:1, 30:1, 35:1, 40:1, 45:1, 50:1, 55:1, 60:1, 70:1, 80:1, 90:1, and 100:1 by volume.

Typical furfural yields with sulfolane as the reaction solvent are about 80% at as high as 99% conversion. Also, certain by-products (e.g., humins) which are soluble in the reaction solvent can be precipitated by addition of water or aqueous solution and then removed by filtration, thereby providing a convenient and effective way of removing these undesirable byproducts from the reaction mixture.

Figure 2:
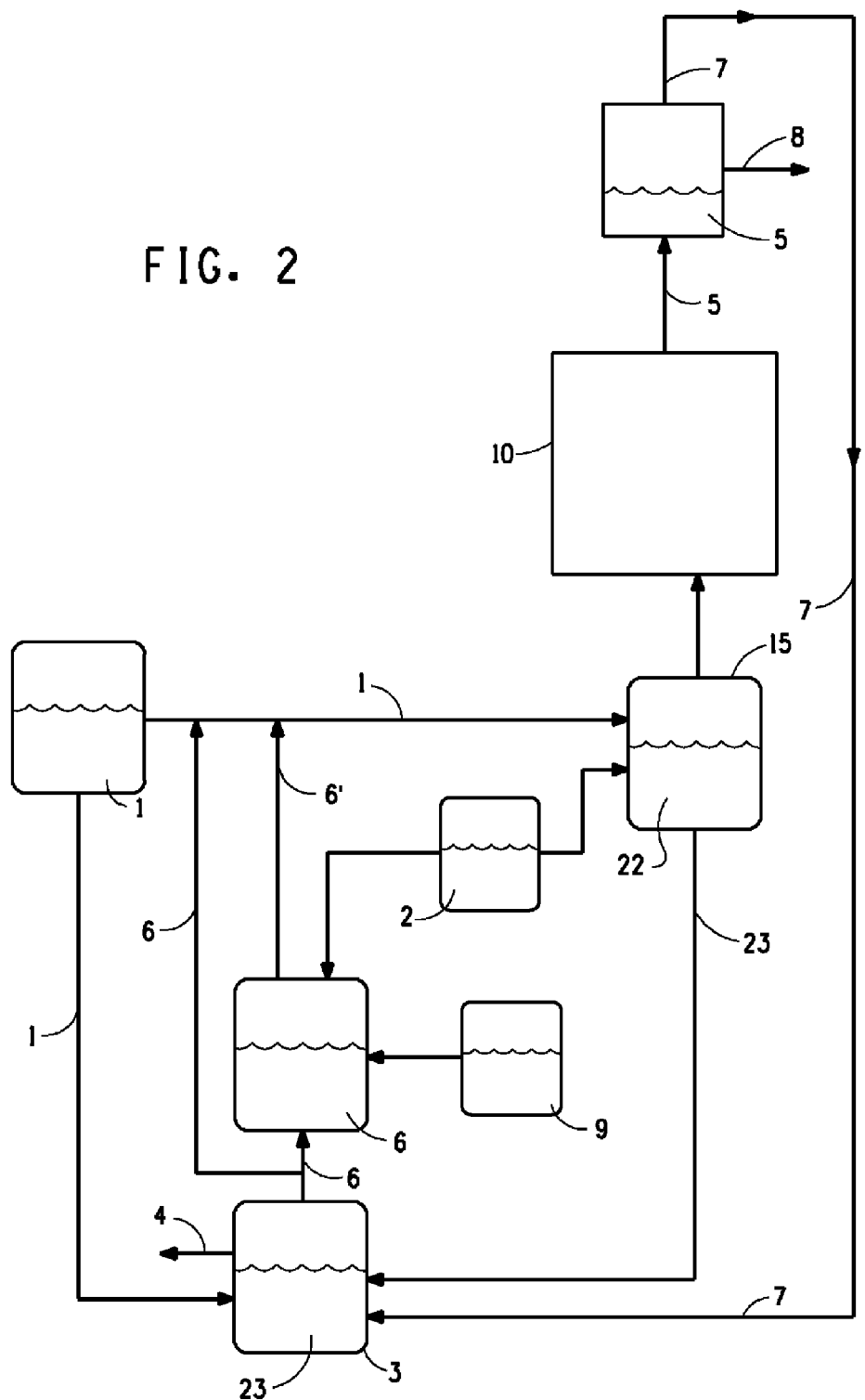
FIG. 2 is a schematic illustration of another exemplary reactor configuration used in the production of furfural in a continuous mode in accordance with various embodiments of the present invention.

In another embodiment of the process described herein, the process is run continuously. FIG. 2 shows a schematic illustration of another exemplary reactor configuration used in the production of furfural in a continuous mode in accordance with various embodiments of the present invention. With reference to FIG. 2, the reaction vessel 15 is charged initially with an acid solution 2 comprising a high boiling, water-miscible solvent and a catalytic amount of soluble acid. The contents of the reaction vessel 15 are heated to the reaction temperature. An aqueous feedstock solution 1 containing $C_5$ and/or $C_6$ sugar solution is added to the hot reaction vessel 15. The sugar undergoes chemical transformation to furfural, which, along with water from the feed and produced by the reaction, is then removed from the reaction mixture 22 via reflux through a multistage distillation column 10 equipped with a condenser. This minimizes the residence time of furfural 8 in the acidic environment and thereby minimizes its degradation. The furfural 8 is separated from the water 7 and purified by any convenient methods known in the art, and the product furfural 8 is isolated. The water 7 is either recycled to the source of the aqueous feedstock solution 1 or can be used in the precipitation of non-volatile reaction by-products or is released from the process At least a portion 23 of the contents of the reaction vessel 15 are diluted with aqueous feedstock solution 1 or water 7 in the mixing zone 3. This initiates precipitation of unwanted byproducts, such as humins 4. The ratio of water or aqueous feedstock solution to reaction vessel contents 23, referred to herein as the "dilution ratio," can be from about 0.5:1 up to 100:1 by volume. In an embodiment, the ratio is from about 1:1 to about 10:1 by volume. Any suitable dilution ratio can be used, as describe supra. The precipitated byproducts 4 are removed by any convenient means, such as filtration or centrifugation. The isolated solids 4 are conveyed to and washed to reclaim any reaction solvent, furfural or sugar that was retained in the wet solids. The solids can be washed with water or with aqueous feedstock solution; washing with feedstock solution allows the desired reclaiming and recycle of solvent and sugars to be achieved without adding additional water to the process.

If necessary, the washed solids are then further dried. Isolated solids can be conveyed and burned as an energy source. The precipitate-free liquid 6 can be returned to the source of the aqueous feedstock solution 1, or into the reaction vessel 15.

The precipitate-free liquid 6 remaining after the solids 4 are removed passes into a pH adjustment chamber in which the pH of the solution is adjusted as needed by adding makeup acid solution 2. This is done to replenish any acid that degrades or is otherwise lost in the process. In an embodiment, the precipitate-free liquid 6 is concentrated by evaporation before mixing with an acid solution 2 or water-miscible organic solvent 9 and the resultant mixture 6' is then mixed with the aqueous feedstock stream to form a pre-mixed feedstock solution 1. The pre-mixed aqueous feedstock solution 1 is finally fed to the reaction vessel 15. The flow of the feedstock 1 can be adjusted partially or completely to go either towards the reaction vessel 15 and mixing with 6 or 6', or can be adjusted to go towards mixing zone 3 to be mixed with solution 23. Thus, a continuous flow of components into and out of the reaction vessel 15 as well as the other components of the process is established, using the feedstock solution 1 and/or water 7 to precipitate and remove humins 4 from at least a portion 23 of the reaction mixture 22 coming from reaction vessel 15, while simultaneously distilling water and furfural out of reaction vessel 15 into distillation column 10. The flow of liquid and solids as indicated by the arrows in FIG. 2 can occur simultaneously with the proper balance of inlet and outlet flows.

The process described above produces furfural from $C_5$ and/or $C_6$ sugars at both high yield and high conversion, without production of insoluble char in the reaction vessel. In an embodiment, the furfural yield is in the range of 15-85% or 45-85% or or 60-85%. In another embodiment, the C5 and or C6 sugar conversion is in the range of 30-100% or 80-100% or 90-100%. The disclosed process is capable of operation in a batch or a continuous mode. The process can be carried out without the need for high pressure equipment. Also, certain by-products (e.g., humins) solubilized in the reaction solvent can be precipitated by addition of water, or aqueous solution and then removed (e.g., by filtration), thereby providing a convenient and effective way of removing these undesirable byproducts from the reaction mixture in both batch and continuous modes of operation.

In one embodiment of the invention disclosed herein, a process is provided comprising the steps of:
 a) providing a water-miscible organic solvent and a soluble acid catalyst in a reaction vessel, wherein the boiling point of the solvent is higher than about 100° C.;
 b) providing an aqueous feedstock solution comprising: at least one $C_5$ sugar, at least one $C_6$ sugar, or a mixture of at least one $C_5$ sugar and at least one $C_6$ sugar;
 c) adding the feedstock solution to the reaction vessel to form a reaction mixture wherein
  i) the temperature of the reaction mixture is between about 100° C. and about 250° C.,
  ii) the reaction mixture pressure is between 0 MPa and about 0.21 MPa, and
  iii) the feedstock, organic solvent, and catalyst are in contact for a time sufficient to effect a reaction to produce furfural and water;
 d) removing vapors of furfural and water from the reaction mixture via reflux through a multistage distillation column;
 e) condensing and collecting a solution of furfural and water; and
 f) recovering the furfural from the collected solution.

In one embodiment of the invention disclosed herein, the contents of the reaction vessel are heated to a temperature between about 100° C. and about 250° C. before step c).

In a further embodiment of the invention disclosed herein, the process further comprises the steps of:
 g) diluting the remaining contents of the reaction vessel, or a portion thereof, in a mixing chamber with water or with an aqueous feedstock solution comprising: at least one $C_5$ sugar, at least one $C_6$ sugar, or a mixture of at least one $C_5$ sugar and at least one $C_6$ sugar, thereby precipitating water-insoluble byproducts;

h) removing the byproducts precipitated in step g), and i) feeding the solution remaining after step h) back to the reaction vessel.

The solution remaining after step h) can be concentrated by evaporation before it is fed back to the reaction vessel.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "invention" or "present invention" is a non-limiting term and is not intended to refer to any single variation of the particular invention but encompasses all possible variations described in the specification and recited in the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

Abbreviations

The meaning of abbreviations is as follows: "BP" means boiling point at 0.101 MPa pressure, "cm" means centimeter(s), "DMSO" means dimethylsulfoxide, "MP" means melting point, "FF" means furfural, "g" means gram(s), "h" means hour(s), "HPLC" means high pressure liquid chromatography, "m" means meter(s), "min" means minute(s), "mL" means milliliter(s), "mm" means millimeter(s), "MPa" means megapascal(s), "PTFE" means poly(tetrafluoroethylene), "rpm" means revolutions per minute, "wt %" means weight percentage, "µL" means microliter(s), and "µm" means micrometer(s).

Materials

Xylose was obtained from Sigma-Aldrich Corporation (St. Louis, Mo.). The following solvents and reagents were obtained from Sigma-Aldrich Corporation (St. Louis, Mo.): sulfolane, PEG (polyethylene glycol) 4600, PEG 10,000, PEG 1000, isosorbide dimethyl ether, propylene carbonate, adipic acid, poly(ethyleneglycol)dimethyl ether, isosorbide, diethylene glycol, bisphenol A, 4-methoxyphenol, ε-caprolactam, 2-pyrrolidinone, catechol, 1H-imidazole, gamma-butyrolactone, 1-methyl-2-pyrrolidiinone, gamma-valerolactone, and dimethylsulfoxide. The following solvents were obtained from E. I. du Pont de Nemours and Co. (Wilmington, Del.): Cerenol™ 250 (poly-1,3-propanediol), and Cerenol™ 1000 (poly-1,3-propanediol). Glycerol was obtained from Avantor Performance Materials (Center Valley, Pa.). Sulfuric acid and phosphoric acid were obtained from VWR International (Radnor, Pa.).

Deionized water was used unless otherwise indicated.

Methods

Distillates and reaction flask contents were analyzed on a calibrated Biorad Aminex HPX-87H HPLC column (Bio-Rad Company) using a refractive index detector, and the column wash was analyzed via gas chromatographic analysis using a flame ionization detector and a calibrated 30 m DB-1 GC column (Agilent Technologies).

Example 1

Furfural Yield in Various Solvents

Solvents used in this example are described in Table 1.

TABLE 1

| Name | CAS Reg. No. | BP (° C.) | MP (° C.) |
| --- | --- | --- | --- |
| Sulfolane | 126-33-0 | 285 | 20 |
| PEG (polyethylene glycol) 4600 | 25322-68-3 | >200 | |
| PEG 10000 | 25322-68-3 | >200 | 63 |
| PEG 1000 | 25322-68-3 | >200 | 39 |
| Isosorbide Dimethyl Ether | 5306-85-4 | 234 | |
| Propylene carbonate | 108-32-7 | 240 | −55 |
| Adipic acid | 124-04-9 | 338 | 154 |
| Poly(ethyleneglycol)dimethyl ether | 24991-55-7 | >250 | |
| Isosorbide | 652-67-5 | >200 | |
| Cerenol ™ 250 (poly-1,3-propanediol) | 345260-48-2 | >200 | |
| Cerenol ™ 1000 (poly-1,3-propanediol) | 345260-48-2 | >200 | |
| Diethylene glycol | 111-46-6 | 245 | −10 |
| Glycerol | 56-81-5 | 290 | 20 |

TABLE 1-continued

| Name | CAS Reg. No. | BP (° C.) | MP (° C.) |
|---|---|---|---|
| Bisphenol A | 80-05-7 | >200 | 156 |
| 4-Methoxyphenol | 150-76-5 | 247 | 55 |
| ε-Caprolactam | 105-60-2 | 270 | 70 |
| 2-Pyrrolidinone | 616-45-5 | 245 | 23 |
| Catechol | 120-80-9 | 245 | 105 |
| 1H-Imidazole | 288-32-4 | 256 | 85 |
| gamma-butyrolactone | 96-48-0 | 205 | −45 |
| 1-methyl-2-pyrrolidiinone | 872-50-4 | 202 | −24 |
| gamma-valerolactone | 108-29-2 | 208 | −31 |

The conversion of xylose to furfural was carried out in a 10 mL three-necked round-bottomed flask (Chemglass, Inc. Life Sciences Catalog No. PN CG-1507-03) equipped with a PTFE-coated magnetic stirring bar (VWR 58949-010), thermowell, and a threaded adapter with cap (Chemglass, Inc. Life Sciences Catalog No. CG-350-10) and a PTFE-lined silicon septum (National Scientific Catalog No. B7995-15). This reaction flask was connected to a vacuum-jacketed Vigreux distillation column (Chemglass, Inc. Life Sciences Catalog No. CG-1242) loaded with 8.0 g of 4 mm diameter glass beads (Chemglass, Inc. Life Sciences Catalog No. CG-1101-03). The beads were held in place at the bottom of the distillation column with a piece of 1/16" (0.159 cm) thick fluoropolymer film that was approximately 3/4" (1.90 cm) wide by 3" (7.62 cm) long that was either wound up into a coil or folded so that it contained pleats. A 20 mL plastic syringe with Luer lock tip (Chemglass, Inc. Life Sciences Catalog No. PN 309661) was connected to 1/16" fluoropolymer tubing which was pierced through the septum. Addition of the xylose solution from the syringe to the reaction vessel was controlled with a digital syringe pump. The reactions were carried out under an atmosphere of nitrogen.

To the reaction flask were added 5 g of solvent and less than 0.15 g of an aqueous solution of sulfuric acid. The syringe on the syringe pump was filled with an aqueous xylose solution which was weighed prior to addition, and then reweighed after the completion of addition to determine the total amount of xylose solution added to the reaction mixture. After the flask was loaded, it was attached to the distillation column, and the 1/16" (0.159 cm) fluoropolymer tube was inserted through the septum and into the solvent, just above the stirring bar. An oil bath was heated to above the desired internal reaction temperature. The flask was lowered into the hot oil to bring the solvent/acid solution to the desired internal reaction temperature, and addition of the xylose solution from the syringe using the syringe pump was started. Xylose solution was added at various rates for a set amount of time, during which the water and furfural were distilled into a weighed collection flask. At the end of the reaction time, the syringe pump was stopped, the tube was pulled from the reaction flask, and the apparatus was raised out of the oil bath.

The amount of distillate collected was weighed and the mixture was diluted with a measured amount of an aqueous dimethylsulfoxide (DMSO) solution of known DMSO concentration, and mixed until it was homogeneous. In reactions with high xylose concentration feed, the furfural separated from the water in the collection flask, and for the purposes of analytical determination of furfural, these two phase mixtures were diluted to the point that all components were miscible. The DMSO was used as an internal standard for quantitation in the analytical methods. The reaction pot was removed from the distillation column and weighed to determine the mass of material remaining in the flask. Another measured amount of an aqueous DMSO solution of known concentration was added to the reaction flask and this was mixed well. The contents of the reaction flask were then transferred to 50 mL centrifuge tubes, the reaction flask was washed thoroughly, and the washes were combined in the 50 mL centrifuge tube. Any solids adhering to the reaction flask walls were scraped from the walls and were also transferred to the 50 mL tube. The solids were centrifuged to the bottom of the tube, and the supernatant was analyzed. The distillation column was then washed with approximately 30-50 mL of water and then an aqueous DMSO solution of known concentration was added to the column wash for analytical purposes.

The distillate and reaction flask contents were then analyzed on a calibrated Biorad Aminex HPX-87H HPLC column using a refractive index detector, and the column wash was analyzed using a calibrated 30 m long DB-1 GC column using flame ionization detection. The furfural distillation yield was determined by the ratio of the moles of furfural detected in the distillate divided by the moles of xylose added into the reaction flask. The total furfural yield was calculated similarly using the combined moles of furfural detected in the distillate, reaction flask and column washes.

Furfural yields for the solvents used are presented in Table 2.

TABLE 2

| Run | Solvent | $H_2SO_4$ (wt %) | Average Internal Reaction Temperature (° C.) | Furfural Distillate yield (%) |
|---|---|---|---|---|
| 1-1 | Sulfolane | 0.1 | 175 | 72 |
| 1-2 | Sulfolane | 0.1 | 174 | 71 |
| 1-3 | Sulfolane | 1.1 | 174 | 70 |
| 1-4 | PEG 4600 | 1.1 | 170 | 67 |
| 1-5 | PEG 10000 | 1.1 | 168 | 65 |
| 1-6 | PEG 1000 | 1.1 | 173 | 63 |
| 1-7 | PEG 1000 | 0.1 | 176 | 51 |
| 1-8 | PEG 1000 | 0.1 | 171 | 47 |
| 1-9 | gamma-valerolactone | 0.4 | 170 | 62 |
| 1-10 | Gamma-butyrolactone | 0.4 | 170 | 52 |
| 1-11 | Isosorbide Dimethyl Ether | 0.1 | 174 | 51 |
| 1-12 | Propylene carbonate | 0.1 | 175 | 46 |
| 1-13 | Propylene carbonate | 1.1 | 175 | 46 |
| 1-14 | Adipic acid | 1.2 | 169 | 43 |
| 1-15 | Poly(ethylene glycol)dimethyl ether | 0.1 | 165 | 42 |
| 1-16 | Isosorbide | 1.2 | 175 | 40 |
| 1-17 | Cerenol ™ 270 | 1.2 | 174 | 37 |
| 1-18 | Cerenol ™ 1000 | 1.1 | 164 | 35 |
| 1-19 | Diethylene glycol | 0.1 | 178 | 34 |

Some solvents give surprisingly high yields of greater than 43% as shown in runs 1-1 through 1-13 in Table 2. Sulfolane gave the highest yields under the conditions tested (70-72%, Runs 1-1 through 1-3). The yield for any particular solvent has not been optimized in this example, and it is likely that for a particular solvent, the yields can be improved by anyone skilled in the art.

Example 2

Furfural Production with Sulfolane as a Solvent

The xylose to furfural conversion was further characterized using sulfolane as the solvent and sulfuric acid as the acid catalyst. A series of experimental runs were carried out using the following variation of conditions: wt % sulfuric acid as a percentage of the weight of sulfolane was from 0.1 to 1.5%;

wt % xylose in water was from 5 to 25%; average reaction temperature during the experiment was from 140 to 190° C.; rate of aqueous xylose solution addition was from 0.1 to 0.4 mL/min.

The following experimental variables were held constant for this set of reactions: The solvent was sulfolane, the mass of solvent was 5 g, the stirring rate was approximately 500 rpm, reaction time was 40 min, and the reaction set up and method of analysis were as described in Example 1.

A xylose solution was added at a defined rate to a reaction vessel containing sulfuric acid and sulfolane at a designated reaction temperature to form a reaction mixture. The reaction mixture was allowed to react for 40 min with distillation, and the distillate was collected and analyzed. The results of several runs varying xylose weight percent, acid weight percent, reaction temperature, and xylose solution addition rate are shown in Table 3.

The results, presented in Table 3, were analyzed to develop the following mathematical model to predict the percent distilled furfural yield when xylose weight percent, acid weight percent, reaction temperature, and xylose solution addition rate are varied within the ranges tested:

$$\text{Predicted \% } FF \text{ yield distilled} = -515 + 90.4(A) + 0.46(A)(B) + 0.00993(B)(C) - 2.22(C)(D) + 0.319(B)(D) - 0.0617(C)^2 - 0.0165(B)^2 + 0.0382(A)(C)^2 - 0.750(A)^2(C)$$

where
A=wt % acid (relative to the sulfolane)
B=Average reaction temperature, ° C.
C=wt % xylose in the aqueous solution being added
D=Rate of addition of the aqueous xylose solution, mL/min Two other duplicate runs were carried out at 1.5 wt % sulfuric acid loading relative to the sulfolane in the reaction, with a reaction temperature of 170° C., and with addition of a 5 wt % xylose solution at 0.40 mL/min (or 0.08 mL/(mL reaction volume)/min). Under these conditions furfural yields of 76 and 77% were achieved. Another experiment was run at 190° C. with 5 wt % xylose added at 0.40 mL/min (or 0.08 mL/(mL reaction volume)/min) with 0.10 wt % sulfuric acid in sulfolane which gave furfural in 80% yield. The conversion of xylose under these reaction conditions was 99%.

TABLE 3

| Wt % $H_2SO_4$ | Wt % xylose | Reaction Temperature (° C.) | Rate (mL/min) | Furfural yield, distillate (%) | Furfural yield, total (%) |
| --- | --- | --- | --- | --- | --- |
| 1.49 | 15.0 | 166 | 0.25 | 67.8 | 72.3 |
| 0.80 | 15.0 | 167 | 0.24 | 69.5 | 75.4 |
| 1.50 | 25.0 | 142 | 0.39 | 41.5 | 45.1 |
| 0.10 | 25.0 | 142 | 0.39 | 16.0 | 18.4 |
| 1.50 | 5.0 | 140 | 0.40 | 69.9 | 79.0 |
| 0.82 | 15.0 | 165 | 0.25 | 69.9 | 76.6 |
| 0.81 | 5.0 | 167 | 0.25 | 72.4 | 80.0 |
| 1.52 | 25.0 | 138 | 0.10 | 39.8 | 59.3 |
| 0.10 | 5.0 | 189 | 0.10 | 63.4 | 81.2 |
| 0.10 | 25.0 | 140 | 0.10 | 17.2 | 27.3 |
| 0.10 | 5.0 | 139 | 0.10 | 28.1 | 50.0 |
| 0.10 | 25.0 | 189 | 0.10 | 63.6 | 75.4 |
| 0.80 | 15.0 | 165 | 0.25 | 69.2 | 76.1 |
| 0.81 | 15.0 | 166 | 0.10 | 63.1 | 77.6 |
| 0.10 | 15.0 | 167 | 0.25 | 67.8 | 78.3 |
| 1.46 | 5.0 | 141 | 0.10 | 59.5 | 81.9 |
| 0.81 | 15.0 | 191 | 0.25 | 70.2 | 75.9 |
| 0.82 | 15.0 | 164 | 0.25 | 68.5 | 75.5 |
| 0.80 | 15.0 | 165 | 0.25 | 71.0 | 78.3 |
| 0.10 | 25.0 | 192 | 0.39 | 59.8 | 63.2 |
| 0.10 | 25.0 | 188 | 0.39 | 59.6 | 62.4 |
| 0.81 | 15.0 | 164 | 0.39 | 72.8 | 77.9 |

TABLE 3-continued

| Wt % $H_2SO_4$ | Wt % xylose | Reaction Temperature (° C.) | Rate (mL/min) | Furfural yield, distillate (%) | Furfural yield, total (%) |
| --- | --- | --- | --- | --- | --- |
| 1.50 | 25.0 | 187 | 0.40 | 65.7 | 71.2 |
| 1.50 | 25.0 | 187 | 0.10 | 58.4 | 68.5 |
| 1.50 | 5.0 | 190 | 0.40 | 73.9 | 77.7 |
| 0.81 | 15.0 | 140 | 0.25 | 50.7 | 62.8 |
| 1.53 | 5.0 | 191 | 0.10 | 59.0 | 72.7 |
| 0.82 | 25.0 | 164 | 0.25 | 65.1 | 74.5 |
| 0.10 | 5.0 | 138 | 0.40 | 30.4 | 34.1 |
| 0.10 | 5.0 | 190 | 0.40 | 79.5 | 84.7 |
| 1.50 | 5.0 | 169 | 0.40 | 76.3 | 80.5 |
| 1.44 | 5.0 | 171 | 0.39 | 77.4 | 82.4 |
| 1.52 | 25.0 | 164 | 0.39 | 61.7 | 66.4 |
| 1.49 | 25.0 | 173 | 0.40 | 55.2 | 57.9 |

Precipitation of Humins from the Reaction Mixture.

The xylose to furfural conversion was carried out using sulfolane as the solvent and sulfuric acid as the acid catalyst using procedures similar to those described in Example 2. Portions (0.25 g) of the reaction mixture containing dissolved humin byproducts were combined with 0.20, 0.79 and 1.18 g of water, respectively, and mixed thoroughly. A dark solid precipitated from each of these mixtures. Each mixture was centrifuged at 14000 rpm to form a solid pellet. The supernatant was removed and the solids were suspended in water, and centrifuged again to form a washed pellet. The supernatant was removed and the solids were dried in a vacuum oven to give 0.0040, 0.0067 and 0.0070 g of solid, respectively. This procedure was repeated in a second set of experiments where 0.25 g portions of the reaction mixture were combined with 0.20, 0.80 and 1.20 g of 20 wt % xylose solution. Using a solid isolation procedure as described above gave 0.0032, 0.0100, and 0.0115 g of dried solids, respectively. This example demonstrates the removal of humins by addition of water, or a solution of C5 sugar to the reaction mixture.

Example 3

Furfural Production with Phosphoric Acid as a Catalyst

The xylose to furfural conversion was carried out using sulfolane as the solvent and phosphoric acid as the acid catalyst using the procedures as described in Example 1. A series of process runs were performed using a wt % of phosphoric acid as a percentage of the weight of sulfolane from 1.3 to 10.3 wt %. The following experimental variables were held constant for this set of reactions: The solvent was sulfolane, the mass of solvent was 5 g, the stirring rate was approximately 500 rpm, reaction time was 20 min, the xylose solution was 5 wt %, the xylose solution rate of addition was 0.4 mL/min, the average reaction temperature during the experiment was between 168 and 171° C., and the reaction set up and methods of analysis were as described in Example 1.

Xylose solution was added at a defined rate to the reaction vessel containing phosphoric acid and sulfolane at a designated reaction temperature to form a reaction mixture. The reaction mixture was allowed to react for 20 min with distillation, and the distillate was collected and analyzed. The results of several runs varying phosphoric acid wt % are shown in Table 4.

TABLE 4

| Wt % Phosphoric Acid | Wt % Xylose | Reaction Temperature (° C.) | Rate (mL/min) | Furfural yield, distillate (%) | Furfural yield, total (%) |
|---|---|---|---|---|---|
| 1.3 | 5.0 | 168 | 0.4 | 20 | 28 |
| 2.7 | 5.0 | 171 | 0.4 | 43 | 55 |
| 4.5 | 5.0 | 170 | 0.4 | 60 | 70 |
| 7.0 | 5.0 | 167 | 0.4 | 60 | 75 |
| 10.3 | 5.0 | 168 | 0.4 | 67 | 70 |

Example 4

Continuous Process for the Production of Furfural

A 50 mL round-bottomed flask with a 29/26 ground glass joint was modified such that three threaded joints were sealed to the flask. Two of these threaded joints (Chemglass, Inc. PN CG-350-10) were used to form a compression seal with lengths of ⅛" (0.318 cm) outer diameter fluoropolymer tubing used in the process. The third joint (Chemglass, Inc. PN CG-350-01) was sealed with a septum, and used as an extra port as needed. The modified flask was loaded with a fluoropolymer-coated magnetic stirring bar, 35 g of sulfolane, and 0.1545 g of sulfuric acid. The flask was connected to a distillation column (Chemglass, Inc. Lifescience Company Catalog No. CG1247-10) containing 165 g of 6 mm diameter glass beads on top of a piece of fluoropolymer film folded to hold the beads in the distillation column. The distillation column was connected to a condenser that was chilled to about 15° C. with a recirculating chiller.

The reaction flask was lowered into a tin/bismuth metal bath heated to 283° C. in order to generate an internal reaction temperature of approximately 180° C. One of the fluoropolymer tubes sealed in one of compression joints had one end submerged in the hot reaction mixture. The other end of this tube was connected to a peristaltic pump (Masterflex PTFE pump head, PN 77390-00) which was removing the reaction mixture away from the reaction flask at approximately 0.4 mL/min; this was pumped through the other end of the tube into a small mixing chamber (Swagelok fitting, PN SS-200-3TFT) containing a small, rotating fluoropolymer-coated magnetic stirring bar. Also pumped into this mixing chamber was a 5 wt % aqueous xylose solution contained in a glass bottle that was placed on a balance and was weighed at the start of the reaction. Over the 17.6 h reaction window described here, 1944 g of the xylose solution (97 g of xylose) was pumped through the small mixing chamber using an HPLC pump (Gilson) at a rate of approximately 2 mL/min or a 5:1 ratio relative to the volume of incoming reaction mixture, thereby initiating precipitation. A back pressure regulator set at 0.21 MPa was installed after the HPLC pump to maintain a constant flow of sugar solution into the small mixing chamber.

After precipitation in the mixing chamber, the water/sulfolane/xylose solution containing suspended humins was transported through a switching valve and into one of four 47 mm stainless steel filter holder assemblies (Pall Corporation). The filter holder assemblies each contained a 1 μm glass filter media which was used to filter the solid. When the back pressure increased to approximately 0.17 MPa because of buildup of solid on the filter media, the switching valve was used to direct the mixture from the mixing chamber to another filtration assembly in order to maintain the system pressure below about 0.17 MPa throughout the run.

The clear filtrate from the filter assembly flowed into a 60 mL screw cap bottle (Wilmad-LabGlass PN LG-4597-098) modified by the addition of a threaded joint (Chemglass, Inc. PN CG-350-01) and a GL-45 cap (Chemglass, Inc. PN CG-1158-20) containing three ports for ⅛" tubing. The bottle sat atop a magnetic stirring plate (IKA) in order to move the fluoropolymer-coated magnetic stirring bar contained in the bottom of the bottle. A pH electrode (Thermo Scientific® Orion PN 911600) was inserted through and sealed with the threaded joint in this bottle. This apparatus was referred to as the pH adjustment chamber. The pH electrode was connected to a pH meter (Eutech Instruments, pH 200 Series) which controlled a micro-pump (Biochem Valve, PN 20SP1210-5TE). The pH meter adjustment level was set to pH=1.9. When the pH in the adjustment chamber climbed above 1.9, the pH meter controlled micro-pump would add one injection of approximately 15 μL of an 8.85 wt % aqueous sulfuric acid solution into the pH adjustment chamber through a 1/16" outer diameter fluoropolymer tube. Additional injections were made as necessary to maintain the pH at 1.9. This was the technique used to control the pH of the process solution coming from the filtration assembly. During the 17.6 h reaction window, 5.47 g of acid solution (a total of 0.48 g of sulfuric acid) was added via the micro-pump into the pH adjustment chamber.

A ⅛" diameter fluoropolymer tube submerged to the bottom of the pH adjustment chamber was connected to a valveless rotating reciprocation pump (pump head was from Fluid Metering Inc., PN RH00, and the drive was from Scilog, Inc.). The filtrate liquid was pulled from the pH adjustment chamber to the pump head and was then pushed through a length of ⅛" diameter fluoropolymer tubing threaded through a compression joint and into the reactor such that the end of the tube was just above the reactor solvent level. The pump was set to deliver approximately 2.4 mL/min from the pH adjustment chamber into the reaction vessel. The total volume of the reaction mixture in the reactor was approximately 25 mL, making the reaction volume to total flow rate ratio equal to 10.4/min (meaning that the reaction volume was 10.4 times as great as the volume flowing into the reactor every minute).

When the pH-adjusted solution containing acid catalyst, xylose, water and sulfolane entered the hot reaction flask, the xylose was converted to furfural which was distilled along with the water through the distillation column and was condensed overhead. The sulfolane and acid remained in the reaction flask and recycle loop during the process. The process was run continuously in the fashion described above with the flow rates as stated. The distillate was collected during this time, and analyzed for furfural. The total amount of furfural collected in the 17.6 hour reaction window was 48.16 g corresponding to a 78% furfural molar yield. The solids collected on the filtration assemblies were washed and dried. The total amount of washed and dried solid collected in 17.6 h was 4.152 g. Of the 17.6 h in which the unit was operated, an apparent steady state operation occurred over the last 10.7 h, during which time the average molar yield of furfural was 81%.

Example 5

Continuous Process for the Production of Furfural

A 500 mL round-bottomed flask with a 29/26 ground glass joint was modified such that three threaded joints were sealed to the flask. Two of these threaded joints (Chemglass, Inc. PN CG-350-10) were used to form a compression seal with lengths of ⅛" (0.318 cm) outer diameter fluoropolymer tubing used in the process. The third joint (Chemglass, Inc. PN CG-350-01) was sealed with a septum, and used as an extra port as needed. The modified flask was loaded with a fluoropolymer-coated magnetic stirring bar, 297 g of sulfolane, and 1.28 g of sulfuric acid. The flask was connected to a distillation column (Chemglass, Inc. Lifescience Company Catalog No. CG1247-10) containing 165 g of 6 mm diameter glass beads on top of a piece of fluoropolymer film folded to hold the beads in the distillation column. The distillation column was connected to a condenser that was chilled to about 15° C. with a recirculating chiller.

The reaction flask was lowered into a tin/bismuth metal bath heated to 218° C. in order to generate an internal reaction temperature of approximately 180° C. One of the fluoropolymer tubes sealed in the compression joint had one end submerged in the hot reaction mixture. The other end of this tube was connected to a peristaltic pump (Masterflex PTFE pump head, PN 77390-00) which was removing the reaction mixture away from the reaction flask at approximately 0.2 mL/min; this was pumped through the tube into a small mixing chamber (Swagelok fitting, PN SS-200-3TFT) which contained a rotating, small fluoropolymer-coated magnetic stirring bar. Also pumped into this mixing chamber was a 10 wt % aqueous xylose solution. This solution was previously placed on a balance and was weighed at the start of the process. Over the 38 h reaction window for which the process was run, 2504 g of the aqueous xylose solution (250.4 g of xylose) was pumped through the small mixing chamber using an HPLC pump (Gilson) at a rate of approximately 1.0 mL/min or a 5:1 ratio relative to the incoming volume of reaction mixture, thereby initiating precipitation of humin byproduct in the mixing chamber. A back pressure regulator set at 0.21 MPa was installed after the HPLC pump to maintain a constant flow of sugar solution into the small mixing chambe.

After precipitation in the mixing chamber, the water/sulfolane/xylose solution containing suspended humin particle byproduct was transported through a switching valve and into either a 142 mm stainless steel filter assembly (Sartorius AG), or one of three 47 mm stainless steel filter holder assemblies (Pall Corporation). The 142 mm filter holder assembly contained a 1 μm polyester filter media (Sefar) which was used to filter the solid. The 47 mm stainless steel filter holders had either 1, 5 or 10 μm filter media made of either polyester or polypropylene filter bag material (Eaton Corporation). When the back pressure increased to approximately 0.17 MPa because of buildup of solid on a filter medium, the switching valve was used to direct the mixture from the mixing chamber to another filtration assembly in order to maintain the system pressure below about 0.17 MPa throughout the process run.

The clear filtrate from the filter assembly flowed into a 60 mL screw cap glass bottle (Wilmad-LabGlass PN LG-4597-098) modified by the addition of a threaded joint (Chemglass, Inc. PN CG-350-01) and a GL-45 cap (Chemglass, Inc. PN CG-1158-20) containing three ports for 1/8" tubing. The bottle sat atop a magnetic stir plate (IKA) in order to rotate a fluoropolymer-coated magnetic stirring bar contained in the bottom of the bottle. A pH electrode (Thermo Scientific® Orion PN 911600) was inserted through and sealed with the threaded joint in this bottle. This apparatus was referred to as the pH adjustment chamber. The pH electrode was connected to a pH meter (Eutech Instruments, pH 200 Series) which controlled a micro-pump (Biochem Valve, PN 20SP1210-5TE). The pH meter adjustment level was set to 2.0. When the pH in the adjustment chamber climbed above 2.0, the pH meter controlled micro-pump added one injection of approximately 15 μL of a 10.0 wt % aqueous sulfuric acid solution into the pH adjustment chamber through a 1/16" outer diameter fluoropolymer tube. Additional injections were made as necessary to maintain the pH at 2.0. This was the technique used to control the pH of the process solution coming from the filtration assembly. During the 38 h reaction window, 11.61 g of acid solution (a total of 1.16 g of sulfuric acid) was added.

A 1/8" diameter fluoropolymer tube submerged to the bottom of the pH adjustment chamber was connected to a valveless rotating reciprocating pump (pump head was from Fluid Metering Inc., PN RH00 and the drive was from Scilog, Inc.). The filtrate liquid was pulled from the pH adjustment chamber to the pump head and was then pushed through a 1/8" diameter fluoropolymer tube into the reactor, just above the solvent level. The pump was set to deliver approximately 1.2 mL/min from the pH adjustment chamber into the reaction vessel. The total volume of the reaction mixture in the reactor was approximately 240 mL, making the reaction volume to total flow rate ratio equal to 200/min (meaning that the reaction volume was 200 times as great as the volume flowing into the reactor every minute).

When the pH-adjusted solution containing acid catalyst, xylose, water and sulfolane entered the hot reaction flask, the xylose was converted to furfural and was distilled along with the water through the distillation column and was condensed. The sulfolane and acid remained in the reaction flask and recycle loop during the process. The process was run continuously in the fashion described above with the flow rates as stated. The distillate was collected and analyzed for furfural. The total amount of furfural collected in the 38 h process run was 126.8 g or 79% furfural molar yield. The solids collected on the filtration assemblies were washed and dried. The total amount of washed and dried solid collected in 38 h was 14.9 g. Of the 38 h in which the unit was operating, an apparent steady state operation occurred over the last 25 h, during which time the average furfural molar yield was 81%.

Example 6

Furfural Production Under Reduced Pressure and Using Sulfuric Acid as a Catalyst The xylose to furfural conversion was further characterized using sulfolane as the solvent and sulfuric acid as the acid catalyst under reduced pressure. A series of experimental runs were carried out under mild vacuum using a J-Kem® Scientific, Inc. vacuum controller to maintain pressure between 0.0067 MPa to 0.101 MPa. The following experimental variables were held constant for this set of reactions: The solvent was sulfolane, the mass of solvent was 5 g, the stirring rate was approximately 500 rpm, reaction time was 40 min, the xylose solution was 5 wt %, the rate of addition of the xylose solution was 0.4 mL/min, the average reaction temperature during the experiment was between 135-140° C., the wt % sulfuric acid as a percentage of the weight of the sulfolane was 1.5% and the reaction set up and method of analysis were as described in Example 1.

Xylose solution was added at a defined rate to a reaction vessel containing sulfuric acid and sulfolane at a designated reaction temperature to form a reaction mixture. The reaction mixture was allowed to react for 40 min with distillation at a controlled pressure, and the distillate was collected and analyzed. The results of several runs varying reaction pressure are shown in Table 5.

TABLE 5

| Pressure (MPa) | Wt % Xylose | Reaction Temperature (° C.) | Rate (mL/min) | Furfural yield, distillate (%) | Furfural yield, total (%) |
|---|---|---|---|---|---|
| 0.101 | 5 | 135 | 0.4 | 72 | 73 |
| 0.080 | 5 | 139 | 0.4 | 72 | 76 |
| 0.053 | 5 | 140 | 0.4 | 74 | 79 |
| 0.027 | 5 | 139 | 0.4 | 76 | 79 |
| 0.0067 | 5 | 140 | 0.4 | 79 | 80 |

Example 7

Furfural Production from Glcose ($C_6$ Sugar) Solution Using Sulfuric Acid as a Catalyst The glucose ($C_6$ sugar; Sigma-Aldrich, Co.) to furfural conversion was run using sulfolane as the solvent and sulfuric acid as the acid catalyst. An experimental run was carried out under the following conditions: The solvent was sulfolane, the mass of solvent was 5 g, the stirring rate was approximately 500 rpm, reaction time was 20 min, the glucose solution was 10 wt %, the rate of addition of glucose solution was 0.4 mL/min, the average reaction temperature during the experiment was 178° C., the wt % sulfuric acid as a percentage of the weight of the sulfolane was 0.4 wt %, and the reaction set up and method of analysis were as described in Example 1.

Glucose solution was added at the defined rate to a reaction vessel containing sulfuric acid and sulfolane at a the reaction temperature to form a reaction mixture. The reaction mixture was allowed to react for 20 min with distillation and the distillate was collected and analyzed. The molar furfural yield contained in the distillate was 21%; levulinic acid remaining in the reaction medium was also produced in this run with a molar yield of 21%, and formic acid was produced in the distillate with a molar yield of 30%.

Comparative Example A

The solvents in this example were tested by the procedures as described above in Example 1. As opposed to those shown in Example 1, these solvents give low yields (<15% yield) to zero percent yield.

TABLE 6

| Run | Solvent | $H_2SO_4$ (wt %) | Average Internal Reaction Temperature (° C.) | Furfural Distillate yield (%) |
|---|---|---|---|---|
| A | 1-methyl-2-pyrrolidinone | 0.4 | 170 | 14 |
| B | Glycerol | 1.2 | 158 | 13 |
| C | Bisphenol A | 0.1 | 174 | 5 |
| D | 4-Methoxyphenol | 0.1 | 175 | 3 |
| E | ε-Caprolactam | 0.1 | 176 | 3 |
| F | 2-Pyrrolidinone | 0.1 | 175 | 3 |
| G | Catechol | 0.1 | 172 | 0 |
| H | 1H-Imidazole | 0.1 | 173 | 0 |

What is claimed is:

1. A process comprising:
   (a) providing a reactor comprising a distillation column disposed on top of a reaction vessel, wherein the reaction vessel contains an acid solution comprising a soluble acid catalyst and a water-miscible organic solvent;
   (b) bringing an aqueous feedstock solution into contact with the acid solution in the reaction vessel for a residence time sufficient to produce a mixture of water and furfural, wherein the aqueous feedstock solution comprises $C_5$ sugar, $C_6$ sugar or a mixture thereof, and wherein the contents of the reaction vessel are at a temperature in the range of 100-250° C. and a pressure in the range of 0.0001-0.21 MPa;
   (c) removing the mixture of water and furfural from the top of the distillation column; and
   (d) adding water or the aqueous feedstock solution to at least a portion of the contents of the reaction vessel comprising organic solvent, acid catalyst, water, unreacted sugars and nonvolatile byproducts to precipitate water-insoluble byproducts and removing the precipitated water-insoluble byproducts,
   wherein the water-miscible organic solvent is sulfolane, polyethylene glycol, isosorbide dimethyl ether, isosorbide, propylene carbonate, poly(ethlyene glycol) dimethyl ether, adipic acid, diethylene glycol, 1,3-propane diol, gamma-butyrolactone, gamma-valerolactone, poly(1,3-propanediol) or a mixture thereof.

2. The process according to claim 1, wherein the process is a continuous process further comprising:
   (e) adding at least one of soluble acid catalyst, water-miscible organic solvent or aqueous feedstock solution to the precipitate-free liquid obtained in step (d) and using it as the aqueous feedstock solution in step (b).

3. The continuous process according to claim 2 further comprising:
   (f) separating furfural from the removed mixture of water and furfural of step (c); and
   (g) using water of step (f) for precipitation of byproducts in (d).

4. The process according to claim 1 further comprising:
   (h) concentrating by evaporation at least a portion of the precipitate-free liquid obtained in step (d) and using it as the aqueous feedstock solution in step (b).

5. The process according to claim 1 wherein the acid solution comprises a mineral acid, a heteropolyacid, an organic acid, or a combination thereof, and the acid catalyst present in a solvent at 0.01-10 weight percent based on the total weight of the acid solution.

6. The process according to claim 1 wherein the acid catalyst is sulfuric acid or phosphoric acid.

7. The process according to claim 1 wherein the combined concentration of $C_5$ sugar and/or $C_6$ sugar in the aqueous feedstock solution is in the range of 1-90 weight percent based on the total weight of the aqueous feedstock solution.

8. The process according to claim 1 wherein the combined concentration of $C_5$ sugar and/or $C_6$ sugar in the aqueous feedstock solution is in the range of 5-35 weight percent based on the total weight of the aqueous feedstock solution.

9. The process according to claim 1 wherein the aqueous feedstock solution comprises xylose, glucose, or a mixture thereof.

10. The process according to claim 1, wherein in step (d) the ratio of the water to the contents of the reaction vessel or the portion thereof, is between 0.5:1 and 100:1 by volume.

11. A process comprising the steps of:
a) providing a water-miscible organic solvent and a soluble acid catalyst in a reaction vessel, wherein the boiling point of the solvent is higher than about 100° C.;
b) providing an aqueous feedstock solution comprising: at least one $C_5$ sugar, at least one $C_6$ sugar, or a mixture of at least one $C_5$ sugar and at least one $C_6$ sugar;
c) adding the aqueous feedstock solution to the reaction vessel to form a reaction mixture wherein
  i) the temperature of the reaction mixture is between about 100° C. and about 250° C.,
  ii) the reaction mixture pressure is between 0 MPa and about 0.21 MPa, and
  iii) the feedstock, organic solvent, and catalyst are in contact for a time sufficient to effect a reaction to produce furfural and water;
d) removing vapors of furfural and water from the reaction mixture via reflux through a multistage distillation column;
e) condensing and collecting a solution of furfural and water; and
f) recovering the furfural from the solution of furfural and water collected in step e), wherein the water-miscible organic solvent is sulfolane, polyethylene glycol, isosorbide dimethyl ether, isosorbide, propylene carbonate, poly(ethylene glycol) dimethyl ether, adipic acid, diethylene glycol, 1,3-propane diol, gamma-butyrolactone, gamma-valerolactone, poly(1,3-propanediol) or a mixture thereof.

12. The process of claim 1 further comprising the steps of:
g) diluting the remaining contents of the reaction vessel, or a portion thereof, in a mixing chamber with water or with an aqueous feedstock solution comprising: at least one $C_5$ sugar, at least one $C_6$ sugar, or a mixture of at least one $C_5$ sugar and at least one $C_6$ sugar, thereby precipitating water-insoluble byproducts;
h) removing the byproducts precipitated in step g), and
i) feeding the solution remaining after step h) back to the reaction vessel.

13. The process according to claim 12 further comprising concentrating by evaporation the solution remaining after step h) before feeding it back to the reaction vessel.

14. The process according to claim 12, further comprising adding water or an aqueous solution to the reaction vessel contents remaining after step d), thereby precipitating water-insoluble byproducts; and removing the precipitated byproducts.

* * * * *